United States Patent
Webb et al.

(10) Patent No.: US 7,353,116 B2
(45) Date of Patent: Apr. 1, 2008

(54) CHEMICAL ARRAY WITH TEST DEPENDENT SIGNAL READING OR PROCESSING

(75) Inventors: Peter G. Webb, Menlo Park, CA (US); Douglas A. Amores, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 212 days.

(21) Appl. No.: 10/633,611

(22) Filed: Jul. 31, 2003

(65) Prior Publication Data

US 2005/0026155 A1 Feb. 3, 2005

(51) Int. Cl.
*G06F 7/00* (2006.01)

(52) U.S. Cl. ............... 702/19; 702/20; 703/11; 707/102

(58) Field of Classification Search ............ 702/19; 435/6; 382/128
See application file for complete search history.

(56) References Cited

U.S. PATENT DOCUMENTS

| | | | |
|---|---|---|---|
| 5,117,354 A | 5/1992 | Long et al. | |
| 5,930,768 A | 7/1999 | Hooban | |
| 6,180,351 B1 * | 1/2001 | Cattell ............ | 435/6 |
| 6,188,783 B1 | 2/2001 | Balaban et al. | |
| 6,282,550 B1 * | 8/2001 | Venkatesan et al. ..... | 707/104.1 |
| 6,344,316 B1 | 2/2002 | Lockhart et al. | |
| 6,355,423 B1 | 3/2002 | Rothberg et al. | |
| 6,399,394 B1 | 6/2002 | Dahm et al. | |
| 6,406,849 B1 | 6/2002 | Dorsel et al. | |
| 2001/0039014 A1 | 11/2001 | Bass et al. | |
| 2004/0218795 A1 * | 11/2004 | Zhou et al. ................. | 382/129 |

FOREIGN PATENT DOCUMENTS

| | | | | |
|---|---|---|---|---|
| EP | 1 162 572 | 12/2001 | | |
| WO | WO 01/27809 | 4/2001 | | |
| WO | WO 01/31333 | * | 5/2001 | ............ 702/19 |
| WO | WO 01/80155 | * | 10/2001 | ............ 702/19 |

OTHER PUBLICATIONS www.biodiscovery.com, CloneTracker Version 2, "Microarray Design and Fabrication Management Software," BioDiscovery, Inc., 2002, 2 pages.

* cited by examiner

*Primary Examiner*—Mary K. Zeman

(57) ABSTRACT

A method in which an array identifier for a chemical array with probes at multiple feature locations is retrieved from a memory or read. The array identifier, a request for a test which requires an instruction on reading or processing the signal data read from the array, and payment information, are all forwarded to a remote location. A method is also provided which includes retrieving an instruction on reading or processing signal data read from a chemical array. This is retrieved from a memory using a test request and which memory carries one or more instructions for the array each retrievable with a different test request. Apparatus and computer program products are further provided.

28 Claims, 4 Drawing Sheets

CHEMICAL ARRAY WITH TEST DEPENDENT SIGNAL READING OR PROCESSING

FIELD OF THE INVENTION

This invention relates to arrays, for example polynucleotide arrays such as DNA arrays, which are useful in diagnostic, screening, gene expression analysis, and other applications.

BACKGROUND OF THE INVENTION

Chemical arrays such as biopolymer arrays (for example polynucleotide array such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers onto a substrate, or by in situ synthesis methods. The in situ fabrication methods include those described in U.S. Pat. No. 5,449,754 for synthesizing peptide arrays, and in U.S. Pat. No. 6,180,351 and WO 98/41531 and the references cited therein for synthesizing polynucleotide arrays. Further details of fabricating biopolymer arrays are described in U.S. Pat. No. 6,242,266, U.S. Pat. No. 6,232,072, U.S. Pat. No. 6,180,351, and U.S. Pat. No. 6,171,797. Other techniques for fabricating biopolymer arrays include known light directed synthesis techniques. Methods for sample preparation, labeling, and hybridizing are disclosed for example in U.S. Pat. No. 6,201,112, U.S. Pat. No. 6,132,997, U.S. Pat. No. 6,235,483, and US patent publication 20020192650.

In array fabrication, the probes formed at each feature is usually are expensive. Additionally, sample quantities available for testing are usually also very small and it is therefore desirable to simultaneously test the same sample against a large number of different probes on an array. These conditions make it desirable to produce arrays with large numbers of very small (for example, in the range of tens or one or two hundred microns), closely spaced features (for example many thousands of features). After an array has been exposed to a sample, the array is read with a reading apparatus (such as an array "scanner") which detects the signals (such as a fluorescence pattern) from the array features. Such a reader should typically have a very fine resolution (for example, in the range of five to twenty microns). The signal image resulting from reading the array can then be digitally processed to evaluate which regions (pixels) of read data belong to a given feature as well as the total signal strength from each of the features. The foregoing steps, separately or collectively, are referred to as "feature extraction".

Given the large number of features that are possible on an array, data can be obtained from a sample relating to a great many genes of the organism from which the sample came. Further, different instructions for processing the same feature data may be used to provide different results. The present invention recognizes though that an array user may only want one or more tests which require data from less than all features or which require only a particular type of processing of acquired data. In this situation the array user may not want to pay for using all of an array or all possible processing methods (for example, different interpretation methods), and further because of privacy concerns may actually want measures taken to avoid generating or disclosing data from array features not needed for any requested tests, or generating any results not requested. The present invention further recognizes that on the other hand, from an array fabricator's perspective, it may be more economical to fabricate a large number of arrays which are all identical and use up all space available and which are capable of providing data for many different tests. At the same time, the array fabricator may wish to have a collection of signal data processing routines which can be run on a same sub-array or the entire array. Thus, it would be desirable to provide a way to reconcile these competing concerns of array fabricators and array users.

SUMMARY OF THE INVENTION

The present invention then, provides in one aspect a method involving the use of an array identifier for a chemical array with probes at multiple features. This identifier can, for example, be retrieved from a memory or read (for example, from an array unit which includes the array and carries the identifier). This array identifier may be forwarded, such as to a remote location, with a request for a test which requires an instruction on reading or processing signal data from the array. For example, the instruction may include a sub-array pattern optionally along with an instruction that for the requested test, only features of the sub-array pattern need be read or that only signal data from such features need be processed. Payment information (which for example, includes user account information) may be forwarded in addition to the array identifier. The required instruction may actually be used at different locations, such as the location at which the signal data was read, or at the remote location in the case where the instruction is for processing signal data which has been forwarded to that location.

The present invention also provides a method which includes retrieving an instruction on reading or processing signal data read from a chemical array, from a memory using a test request. The memory may carry one or multiple instructions for one or more arrays, each retrievable with a different test request.

Apparatus and computer program products which can execute a method of the present invention are further provides.

Different embodiments of the present invention may provide any one or more of the following, or other, useful benefits. For example, only data may be acquired or processed from feature locations on an array which are relevant to the one or more requested tests. Any data from array features or data processing which is irrelevant to the requested test may be avoided or segregated. Further, a user can relatively simply pay, and be charged for, only that part of an array or for an evaluation relevant to the one or more requested tests.

BRIEF DESCRIPTION OF THE DRAWINGS

Embodiments of the invention will now be described with reference to the following drawings in which.

Figure 1:
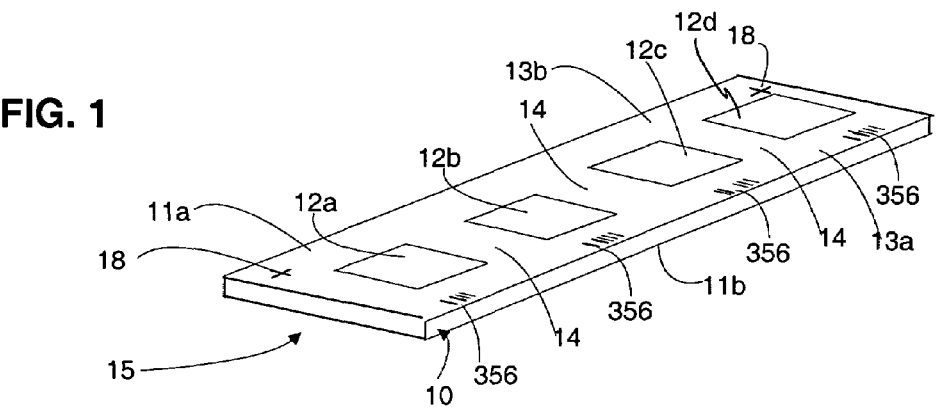
FIG. 1 illustrates a substrate carrying multiple arrays, such as may be read by a method of the present invention.

To facilitate understanding, identical reference numerals have been used, where practical, to designate the same elements which are common to different figures. Drawings are not necessarily to scale. Throughout this application any different members of a generic class may have the same reference number followed by different letters (for example, arrays 12a, 12b, 12c, and 12d may generically be referenced as "arrays 12")

DETAILED DESCRIPTION OF EMBODIMENTS OF THE INVENTION

Throughout the present application, unless a contrary intention appears, the following terms refer to the indicated characteristics.

A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source.

A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

An "oligonucleotide" generally refers to a nucleotide multimer of about 10 to 100 nucleotides in length, while a "polynucleotide" includes a nucleotide multimer having any number of nucleotides.

A chemical "array", unless a contrary intention appears, includes any one, two or three-dimensional arrangement of addressable regions bearing a particular chemical moiety or moieties (for example, biopolymers such as polynucleotide sequences) associated with that region. For example, each region may extend into a third dimension in the case where the substrate is porous while not having any substantial third dimension measurement (thickness) in the case where the substrate is non-porous. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature may incidentally detect non-targets of that feature). An array feature is generally homogenous in composition and concentration and the features may be separated by intervening spaces (although arrays without such separation can be fabricated). In the case of an array, the "target" will be referenced as a moiety in a mobile phase (typically fluid), to be detected by probes ("target probes") which are bound to the substrate at the various regions. However, either of the "target" or "target probes" may be the one which is to be detected by the other (thus, either one could be an unknown mixture of polynucleotides to be detected by binding with the other).

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

"Hybridizing" and "binding", with respect to polynucleotides, are used interchangeably.

A "plastic" is any synthetic organic polymer of high molecular weight (for example at least 1,000 grams/mole, or even at least 10,000 or 100,000 grams/mole.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

When one item is indicated as being "remote" from another, this is referenced that the two items are at least in different buildings, and may be at least one mile, ten miles, or at least one hundred miles apart. When different items are indicated as being "local" to each other, they are at least in the same building and may be in the same room of a building. "Communicating", "transmitting" and the like, reference conveying data representing information as electrical or optical signals over a suitable communication channel (for example, a private or public network, wired, optical fiber, wireless radio or satellite, or otherwise). Any communication or transmission can be between devices which are local or remote from one another. "Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless). "Receiving" something means it is obtained by any possible means, such as delivery of a physical item (for example, an array or array carrying package). When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

When two items are "associated" with one another they are provided in such a way that it is apparent one is related to the other such as where one unambiguously references the other. For example, an array identifier can be associated with an array by being on the array unit (such as on the substrate or housing) that carries the array or on or in a package or kit carrying the array unit. Similarly, a test request can be associated with an array and array identifier by being provided in a same package with them. Another means of association is by means of a common medium (such as paper) carrying both the test request and the array identifier, with the medium being in a same package as the array or with the array identifier also being carried on the array unit. Items of data are "linked" to one another in a memory when a same data input (for example, filename or directory name or search term) retrieves those items (in a same file or not) or an input of one or more of the linked items retrieves one or more of the others. In particular, when an array layout is "linked" with an identifier for that array, then an input of the identifier into a processor which accesses a memory carrying the linked array layout retrieves the array layout for that array. Similarly, an array identifier, test request and the sub-array pattern may be linked in memory by an input of two of them (such as the array identifier and the test request) retrieves the other (such as the sub-array pattern).

A "computer", "processor" or "processing unit" are used interchangeably and each references any combination of hardware or software which can control components as required to execute recited steps and includes. For example a computer, processor, or processor unit includes a general purpose digital microprocessor suitably programmed to perform all of the steps required of it, or any hardware or software combination which will perform those or equivalent steps. Programming may be accomplished, for example, from a computer readable medium carrying necessary program code (such as a portable storage medium) or by communication from a remote location (such as through a communication channel).

A "memory" or "memory unit" refers to any device which can store information for retrieval as signals by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

An array "unit" may be the array plus only a substrate on which the array is deposited, although the assembly may be in the form of a package which includes other features (such as a housing with a chamber). "Array unit" may be used interchangeably with "array assembly".

"Signal data" for a chemical array is data read from one or multiple features of the array such as in a chemical array reader. Signal data for an array or part of the array (that is, for a pattern of less than all the feature locations such as a sub-array pattern) may be referenced as a "signal image". A signal image may exist solely as a signal data in a memory but may be presented on a display or some other device for human viewing if desired.

"Reading" signal data from an array refers to the detection of the signal data (such as by a detector) and the saving of that data in a memory (whether for relatively short or longer terms).

"Processing" signal data read from an array (sometimes referenced as "array signal data" or the like) refers to any method of selecting, modifying, examining or evaluating the signal data, which is normally executed by a processor such as on digital signal data (although analog processes could be used). For example, selecting signal data for features which are within a sub-array and rejecting signal data outside the sub-array. Evaluating array signal data references any method of evaluating the significance of any such data. For example, feature extraction. Interpreting signal data refers to an attempt to understand the significance or meaning of signal data from array features. For example, making a determination of expression of a gene or change in expression in a sample, a determination of gene copy number in a sample, or a determination as to the likelihood that the sample indicates the presence of a pathogen or disease in an organism from which it was derived.

A "package" is one or more items (such as array units optionally with other items) all held together (such as by a common wrapping or protective cover or binding). Normally the common wrapping will also be a protective cover (such as a common wrapping or box) which will provide additional protection to items contained in the package from exposure to the external environment. In the case of just a single array unit a package may be that array unit with some protective covering over the array unit (which protective cover may or may not be an additional part of the array unit itself).

"Sub-array" references a collection of features of the array which are less than all the features of the array (for example, less than 90%, 80%, 60%, 50%, 30%, or 10% of all array features). A "sub-array pattern" is the identification of such features (that is, the pattern in which they are arranged). While features of a sub-array will often be a contiguous set of array features (in the sense that there are no intervening non-sub-array features within the boundaries of the sub-array), this is not necessarily the case and the sub-array pattern can be any arrangement of less than all array features desired. An array may have more than one sub-array pattern, which may or may not overlap with one another. A feature "outside" any sub-array pattern is one which is not a feature of any sub-array pattern.

A "test request" references a type of test which it is desired be performed. The test type may be for testing a sample to ascertain whether it contains certain components quantitatively or qualitatively, such as nucleic acids or peptides or classes of the foregoing, or whether the sample or an organism from which it was derived exhibits a particular condition (for example, the activity of a gene or classes of genes, the presence of particular polymorphisms or class of polymorphisms, or a particular disease condition). A test request can be in any form such as human or machine readable and may or may not actually contain one or more details of the test type itself (for example, the test request may only be an indicator, such as alphanumeric code or other identification of a test type).

When a pattern is "retrieved", this references that the pattern may be expressly or implicitly retrieved. For example, a pattern of particular feature locations may be retrieved from a memory by expressly retrieving an identification of those feature locations or a boundary (or boundaries) encompassing those feature locations. Alternatively, the pattern of particular features may be implicitly retrieved by retrieving an identification of all feature locations outside the pattern, and the pattern feature locations unambiguously derived from that retrieval as all other feature locations of the array. Express retrieval of sub-array patterns will generally be simpler. In the case of patterns of feature locations that are to be rendered incapable of incapable of providing signal data representative of binding of a sample component, it may often be simpler to retrieve these implicitly by retrieving all desired sub-array patterns then deriving the pattern of the features to be rendered incapable as all other array feature locations which are outside any retrieved sub-array pattern.

"Payment information" includes any information which causes a charge to be made to an account (such as a transfer of a currency amount or an increase in a credited or amount) or a request for payment generated (such as a request for transfer of currency or a bill). For example, payment information may include information on an account (such as a credit or debit card number) to which payment will be charged, or a user's identity or location. Payment information could include or consist of an array identifier or part of an array identifier where that array identifier is then used to identify an account to which payment will be charged. For example, an array fabricator could simply keep a record (for example, in a computer memory) of the identification of users to which arrays carrying different array identifiers are shipped along with linked account information for those users. When the fabricator receives a communication of the identifier that identifier (or a part of it) is used by the fabricator (typically by a computer) to retrieve the linked user identification and account information from the memory.

Any recited method herein can be executed at a same location, for example, a first station (which may be a user station) where the array identifier and signal data may be read, or a second station where the instruction is retrieved. Any stations referenced herein may all be remote from one another or all of them or any combination of them can be local (with the rest remote therefrom).

It will also be appreciated that throughout the present application, that words such as "front", "back", "top", "upper", and "lower" are used in a relative sense only.

"May" refers to optionally.

When two or more items (for example, elements or processes) are referenced by an alternative "or", this indicates that either could be present separately or any combination of them could be present together except where the presence of one necessarily excludes the other or others.

Any recited method can be carried out in the order of events recited or in any other order which is logically possible. Reference to a singular item, includes the possibility that there are plural of the same item present. All patents and other references cited in this application, are incorporated into this application by reference except insofar as anything in those patents or references, including definitions, conflicts with anything in the present application (in which case the present application is to prevail).

In methods of the present invention, the signal data from the array may be read or processed at a first location from which the array identifier, the test request, and any payment information, are forwarded to a second location (which may be remote from the first location). The instruction can then be retrieved at the second location from a memory using at least the test request and optionally also the array identifier, where the memory may contain different instructions each retrievable with a different combination of array identifier and test request.

In a first embodiment the method may also include receiving at the first location from the second location the instruction for reading or processing the signal data read from the array. In this embodiment the method may further include at the first location, actually reading the signal data from the array or processing read signal data from the array, either one in accordance with the received instruction.

In a second embodiment where data will be processed at the second location, the method may also include forwarding the read signal data from the first location to the second location (where the signal data may have been read at the first location or elsewhere). In this case in response to the forwarding of the array identifier, test request, read signal data and any payment information to the remote location, a result is received at the first location from the second location. While in the first embodiment this retrieved instruction may be used at the first location for reading or processing the signal data read from the array as already mentioned, in the second embodiment the result received from the remote location may have been generated there based on this retrieved instruction In either embodiment the method may include, at the first location, reading signal data from the array, or exposing the array to a sample. As well, in either situation the instruction may include a sub-array pattern which is used to mask features from which signal data is to be read and saved, or which signal data will be processed using a same signal processing method.

In the first embodiment, where the instruction is used at the first location, masking may be the result of reading array signal data in accordance with the received instruction. One way to achieve this is by not acquiring a signal from feature locations outside any or all retrieved sub-array patterns (that is, signal data may be acquired only from features of the retrieved sub-array patterns). For example, signal data may be acquired from feature locations of each sub-array by illuminating those locations with an interrogating light and detecting any light emitted in response to the interrogating light. In this case no signal data is acquired from feature locations outside any or all retrieved sub-array patterns as a result of not illuminating such feature locations with the interrogating light. In another example which can be used at the first or second location in the first embodiment, or the second location in the second embodiment, feature locations of one or more sub-arrays may be selected as a result of the feature locations outside such sub-arrays being masked during data handling. For example, in such technique signal data may be acquired from both the one or more sub-array feature locations as well as feature locations outside the one or more sub-arrays. However, acquired signal data from the sub-array feature locations is saved in a memory while acquired signal data for feature locations outside any or all retrieved sub-arrays is not saved in the memory. Note that this technique allows for all acquired signal data to be temporarily saved in a memory (for example, a volatile memory) while only the signal data from retrieved sub-arrays features is saved in another memory (for example, a more permanent non-volatile memory).

In another masking technique the method includes applying a same signal processing method only to acquired signal data from features of one or more retrieved sub-array patterns (for example, a different signal processing technique or no signal processing technique may be applied to features outside any or all retrieved sub-array patterns). One example of the foregoing is where the same signal processing method includes an encryption method based on a key, in which case the method may additionally include applying an encryption method based on a different key to signal data acquired from features outside any or all retrieved sub-array patterns. A second example is applying different signal processing methods to acquired signal data from features of different retrieved sub-array patterns. In this second example results from the application of such different signal processing methods may be independent such that a result from one sub-array cannot be derived from a result from one or more other sub-arrays. Furthermore, such results from applying the different signal processing methods may be forwarded to different locations. Further, some such results from applying different signal processing methods may be rejected based on a comparison of those results (that is, with one another) or a comparison of a characteristic of the feature locations in the different sub-arrays (for example, results from sub-arrays having a higher proportion of feature locations producing a weak signal may be rejected).

In methods of the present invention the array may have been exposed to a sample obtained from an individual, in which case the instruction may be retrieved also using an identification of the individual. For example, where a test request is for a test the results of which are dependent upon known genetic polymorphisms and the array contains features for the different polymorphic variants of one or more genes, different sub-array patterns may be retrieved each with probes for the different variants depending upon the identity of the individual (for example, racial characteristics or a unique identifier for that individual which can be used to retrieve information stored in a database on which variants are relevant to that individual). In addition any result generated (for example, at the first or second location) may be one which does not provide any indication of which feature locations of the array bound to a sample component. For example, the result may just state that an organism from which a sample was derived and which sample was exposed to the array, likely does or does not exhibit a particular condition (for example, a disease, presence of a pathogen, particular genetic deficiency, and the like).

As previously mentioned, the instruction may include an instruction on processing read signal data, for each particular array identifier/test request combination which may be retrieved. Such an instruction may include data processing instructions in the form of computer program code (such as a program module), or one or more parameters for a computer program which performs array signal data processing (such as array signal data interpretation). Examples of array signal data processing programs include those which direct a weighing of the significance of read data signals from particular array features. Alternatively, parameters may be provided for any such a module (for example, the weighing factors). In any event, the method may further include performing the processing of the read signal data based on the retrieved instruction. Further, any method of the present invention may include receiving (for example, at the first location) a quoted price for the test requested, or forwarding (for example, from the remote location which forwards the instruction) such a quoted price. Additionally, the method may include charging a user account for which account information was received, with an amount based on the test request received with the account.

The sequence of events in any method of the present invention (for example, any method executed at a station or location) may be repeated one or more times using different test requests for a same array, as well as different combinations of array identifiers and test requests (such as where there are multiple possible test requests for each of those arrays). In this case, a different instruction may be retrieved from memory at the remote location. Either the retrieved different instruction or different results based upon the different retrieved instructions may then be received at the first location for each different test request or different combination of array identifier and test request. Furthermore, Apparatus of the present invention may include an array reader which reads signal data from the array, and a processor which causes the apparatus to execute a method as described herein. The array reader may include a light source to illuminate array feature locations with an interrogating light, as well as a detector to detect light emitted in response to the interrogating light. Computer program products of the present invention may include a computer readable medium carrying a computer program which when loaded into a computer executes a method as described herein.

Figure 2:
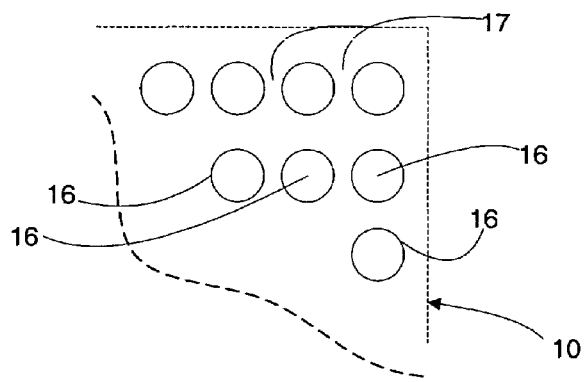
FIG. 2 is an enlarged view of a portion of FIG. 2 showing multiple spots or features of one array.
Figure 3:
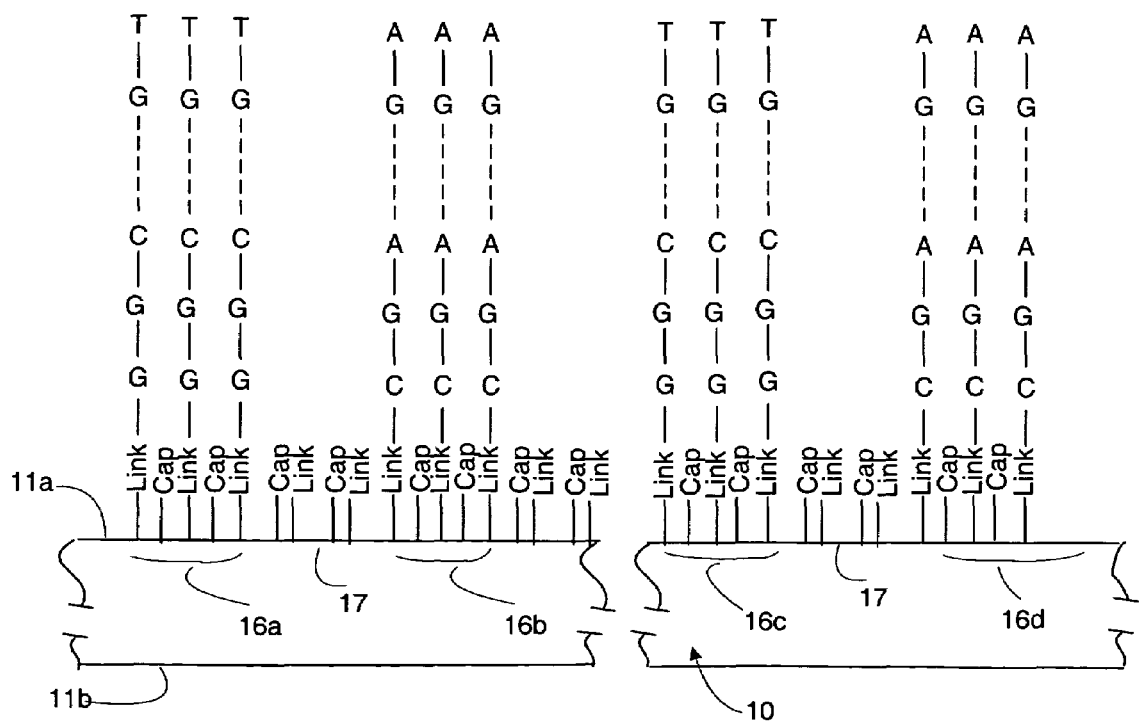
FIG. 3 is an enlarged illustration of a portion of the substrate of FIG. 1.

Referring now to FIGS. 1-3, an array assembly 15 (which may also be referenced as an "array unit") which can be used in methods and apparatus of the present invention, includes arrays 12 which may be read to obtain an array signal image used in methods of the present invention. Substrate 10 may also be in the form of an a rigid substrate 10 (for example, a transparent non-porous material such as glass or silica) of limited length, carrying one or more arrays 12 disposed along a front surface 11a of substrate 10 and separated by inter-array areas 14. Alternatively, substrate 10 can be flexible (such as a flexible web). The substrate may be of one material or of multi-layer construction. Substrate 10 is typically non-porous, and may be smooth and planar, or have irregularities, such as depressions or elevations (although irregular substrate surfaces may make reading of the exposed array more difficult). However, even a flat planar substrate 10 may have small irregularities in its shape (for example, front side 11a may be slightly bent or bowed). A back side 11b of substrate 10 does not carry any arrays 12. The arrays on substrate 10 can be designed for testing against any type of sample, whether: a trial sample; reference sample; a combination of the foregoing; or a known mixture of polynucleotides, proteins, polysaccharides and the like (in which case the arrays may be composed of features carrying unknown sequences whose presence is to be determined). While four arrays 12 are shown in FIG. 1, it will be understood that substrate 10 may use any number of desired arrays 12 such as at least one, two, five, ten, twenty, fifty, or one hundred (or even at least five hundred, one thousand, or at least three thousand). When more than one array 12 is present they may be arranged end to end along the lengthwise direction of substrate 10. Depending upon intended use, any or all of arrays 12 may be the same or different from one another and each will contain multiple spots or features 16 of biopolymers in the form of polynucleotides.

A typical array 12 may contain more than: ten, one hundred, one thousand, or ten thousand features. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature of the same composition are excluded, the remaining features may account for at least 5%, 10%, or 20% of the total number of features). The features may have a maximum dimension of between 20 (or 50) to 100 (or 80) microns and be spaced apart by less than 130 microns (or by less than 100 or 50 microns). Various feature densities on the substrate surface are possible. For example, features having a maximum dimension greater than any of the foregoing figures may be present on the surface of at least 30 features/mm$^2$, 40 features/mm$^2$, or 60 features/mm$^2$. While round features 16 are shown, various other feature shapes are possible (such as elliptical). The features 16 may also be arranged in other configurations (for example, circular) rather than the rectilinear grid illustrated. Similarly, arrays 12 on a same substrate 10 need not be laid out in a linear configuration.

Each array 12 may cover an area of less than 100 cm$^2$, or even less than 50 cm$^2$, 10 cm$^2$ or 1 cm$^2$. In many embodiments, particularly when substrate 10 is rigid, it may be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. When substrate 10 is flexible, it may be of various lengths including at least 1 m, at least 2 m, or at least 5 m (or even at least 10 m). With arrays that are read by detecting fluorescence, the substrate 10 may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically be present which do not carry any polynucleotide. It will be appreciated though, that the interfeature areas 17 could be of various sizes and configurations. Further, such interfeature areas 17 need not be present at all (such as when arrays are fabricated using light directed synthesis techniques). Where interfeature areas 17 are present, the features 16 may be spaced apart by a distance greater than 0 and less than 70%, 60% 50%, 25%, or 10% of a maximum dimension of the feature. Each feature 16 carries a predetermined polynucleotide (which includes the possibility of mixtures of polynucleotides). As per usual, A, C, G, T represent the usual four nucleotides. "Link" (see FIG. 3 in particular) represents a linking agent (molecule) covalently bound to the front surface and a first nucleotide, as provided by a method of the present invention and as further described below. The Link serves to functionalize the surface for binding by the first nucleotide during the in situ process. "Cap" represents a capping agent. The Link may be any of the "second silanes" referenced in U.S. Pat. No. 6,444,268 while the Cap may be any of the "first silanes" in that patent. However, different linking layer compositions than those silanes could be used. As already mentioned, the foregoing patents are incorporated herein by reference, including for example the details of the linking layer compositions used therein.

Substrate 10 also has one or more array identifiers 356 each in the form of a bar code. Identifiers 356 may be associated with an array by being: directly printed onto the substrate 10 or a housing (not shown) carrying substrate 10; printed onto labels attached to substrate 10 or a housing carrying substrate 10; contained in a memory (for example, a solid state memory) attached to substrate 10 or a housing carrying substrate 10; or be provided on a printed label or paper or some other medium or in a memory, any of which is received in or on a same package containing the array unit 15 (and therefore also containing substrate 10). Identifiers such as other optical or magnetic identifiers could be used instead of bar codes, and which will carry the information discussed below. Each array identifier 356 may be associated with its corresponding array by being positioned adjacent that array 12 on the same substrate 10. However, this need not be the case and array identifiers 356 can be positioned elsewhere on substrate 10 if some other means of associating each identifier 356 with its corresponding array 12 is provided (for example, by relative physical locations). Further, a single identifier might be provided which is associated with more than one array 12 on a same substrate 10 and such one or more identifiers may be positioned on a leading or trailing end of substrate 10. Each identifier 356 may also be associated with an array by being in or on a same package or kit which contained by the array and is received by a user. The substrate may further have one or more fiducial marks 18 for alignment purposes during array fabrication or reading.

FIGS. 2 and 3 illustrate ideal features 16 of an array 12 where the actual features formed are the same as the target (or "aim") features, with each feature 16 being uniform in shape, size and composition, and the features being regularly spaced. Such ideally shaped features may not always be possible to obtain but this is not critical in any event. Suitable drop deposition methods for fabricating arrays 12 include those as described in U.S. Pat. No. 6,180,351, U.S. Pat. No. 6,242,266, U.S. Pat. No. 6,306,599, and U.S. Pat. No. 6,420,180. As mentioned above, the foregoing references are incorporated herein by reference particularly as relates to the in situ fabrication apparatus and methods disclosed therein. Alternatively, arrays 12 can be fabricated by known light directed synthesis methods.

Figure 4:
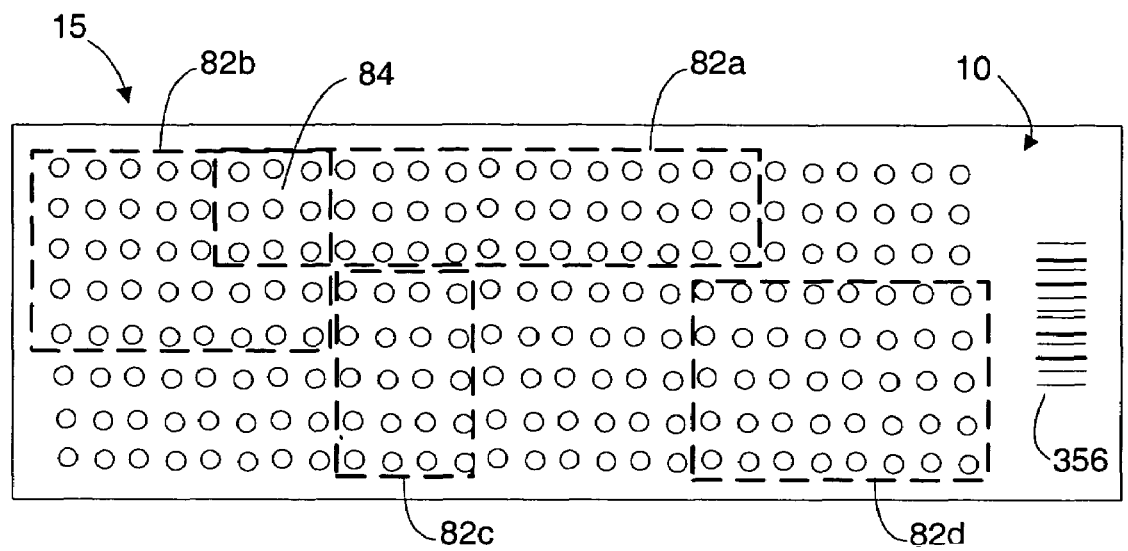
FIG. 4 illustrates the division of a single array into multiple sub-array patterns each of which may be retrievable from a memory using a combination of array identifier and test request.

FIG. 4 shows an array unit 15 carrying a single array 12 and illustrates multiple sub-array patterns 82a through 82d each consisting of features 16 within the boundaries of each pattern 82 shown. Note that sub-arrays 82a, 82b overlap with each other. Each such pattern 82 will include features which are useful for at least one test, for example a test for expression level of certain genes or a class of genes, a test for gene polymorphisms, a test for copy number of a gene or class of genes, a test for the presence of a pathogen, or a test for a disease condition of an organism from which the sample exposed to the array was derived.

Figure 5:
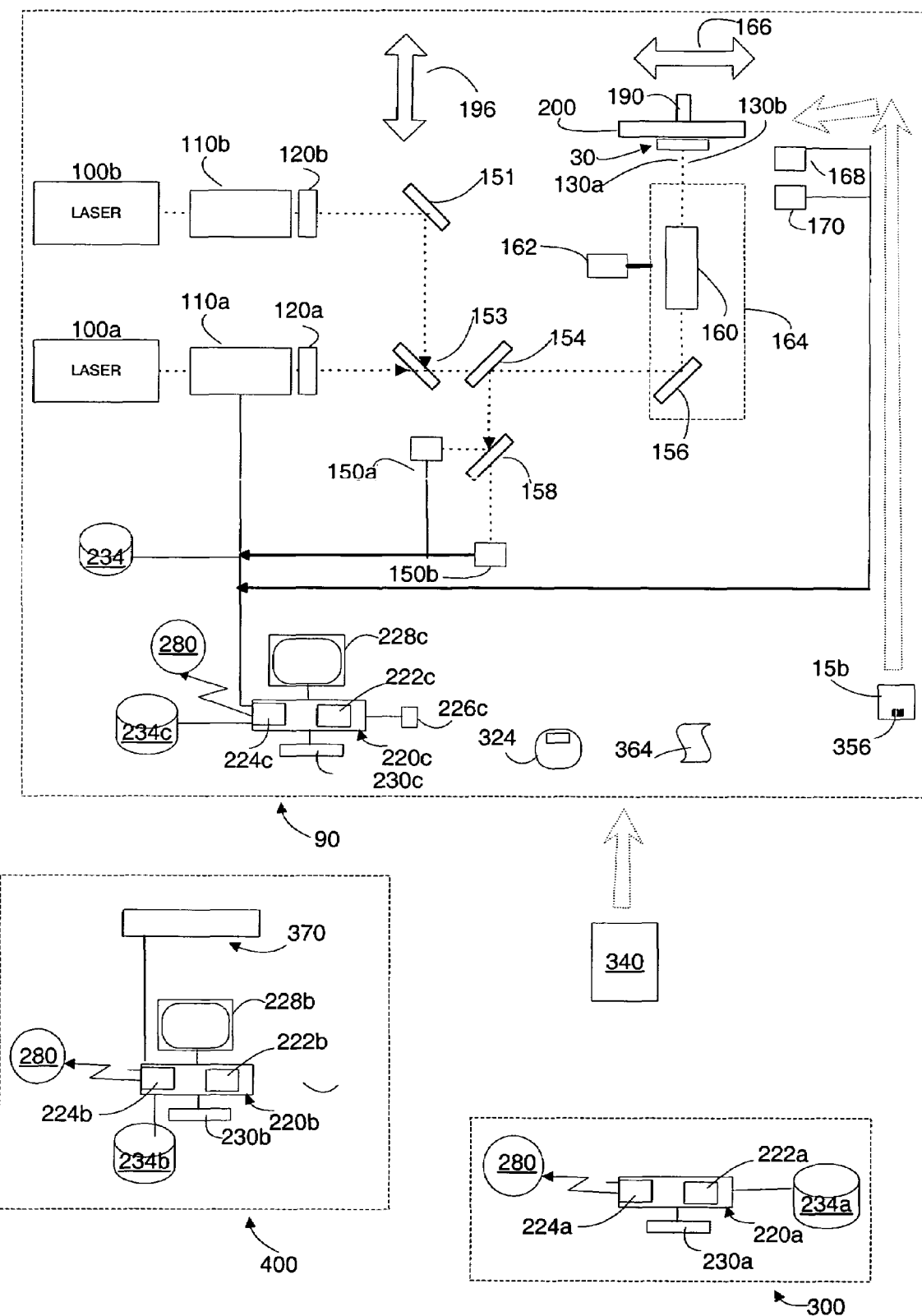
FIG. 5 is a schematic diagram illustrating a reader station, stand-alone station, and central data station, all of the present invention, and their interaction.
Figure 6:
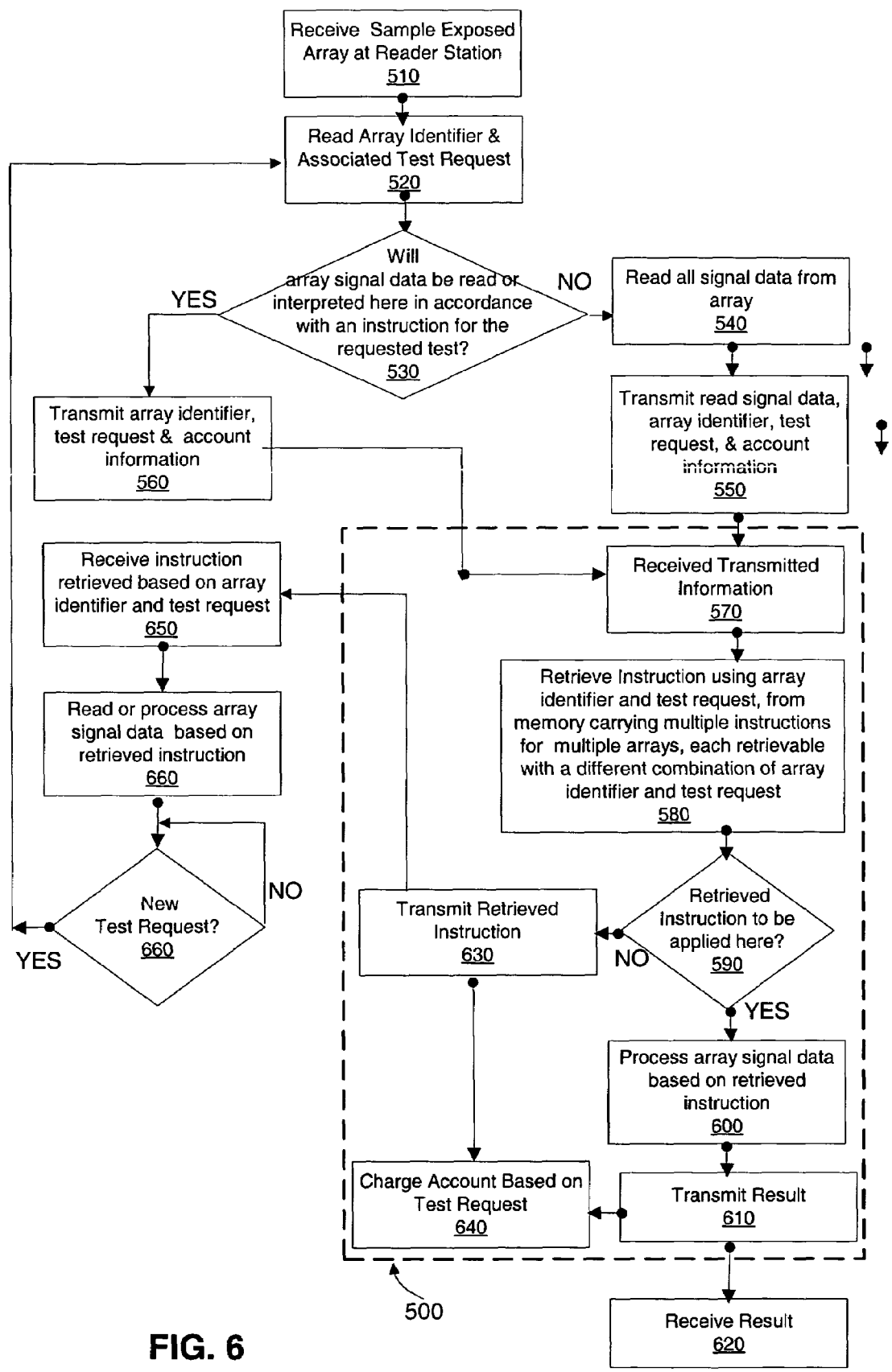
FIG. 6 is a flowchart illustrating methods of the present invention.

The actual patterns 82 (in this case the boundaries defining each sub-array) are not visible on array 12 in FIG. 4, but instead are stored as boundary location data in a memory 234a of a central data station 300 (see FIG. 5) each linked with a different test request and all linked with the array identifier 356 of FIG. 4. Memory 234a will typically store multiple instructions, such as sub-array patterns, for each of multiple different arrays having different array layouts, the instructions for each array each linked with a different test request and all linked with the identifier for that array. In this way any instruction (such as a saved sub-array pattern) for any array can be retrieved from the memory 234a with a different combination of the array identifier and test request. Referring to FIG. 5, central data station 300 also includes a processor 220a which has access to memory 234a and a communication module 224a through which it may communicate with a remote site through a communication channel 280 (such as a network, for example the internet, a telephone network, a WAN or LAN, or satellite link). Processor 220a also has access to a media reader/writer 222a which can read and write to a removable portable memory 324 (such as a magnetic or optical disk, or solid state memory) and may receive operator input through input device 230a (which may be a keyboard, mouse, voice command module, or other devices). In an alternative arrangement, all the instructions for a given array and their linked test requests and array identifier can be saved in, and retrieved from, portable memory 324. In any event, such information can be stored in memory 234a or portable memory 324 either at the time of fabrication of an array 12 or later (for example, it may be learned later that a new instruction for an array is useful to provide an additional test). Data station 300 is "central" in the sense that it may receive requests for an instruction from many remote and/or local (that is, non-remote) locations. Data station 300 may or may not be local to an array fabrication station.

The apparatus in FIG. 5 further illustrates a user station in the form of an array reader station 90. Reader station 90 may sometimes be referenced as an array "scanner". In FIG. 5, a light system provides coherent light from a laser 100 which passes through an electro-optic modulator (EOM) 110 with attached polarizer 120. Each laser 100a, 100b may be of different wavelength (for example, laser 100a providing red light with a peak emission at 630 nm, and laser 100b providing green light with a peak emission at 530 nm) and each has its own corresponding EOM 110a, 110b and polarizer 120a, 120b. The resulting light beams are coherent and monochromatic.

The red interrogating light beam originating from laser 100a is directed along path 130a while the interrogating green beam originating from laser 100b is directed along respective paths 130b. Light is directed along all of the paths 130a, 130b by means of full mirror 151, dichroic mirror 153, and full mirror 156 onto two different locations of an array being read (namely an array 12 of an array unit 15 mounted on holder 200), using optical components in beam focuser 160. Note though that FIG. 5 shows the paths 130a, 130b of the two beams as being coincident up until the position of a mirror 158, for the sake of simplicity. The angle of separation of the beams may be such that each interrogating light beam is directed along a corresponding path 130a, 130b toward front surface 11a at an angle equal that is greater than or equal to 0 degrees and up to 45 degrees to a normal to the back surface (for example less than 1 degree, such as 0.5 degrees). Such an arrangement allows the two interrogating light beams to pass through the same optical system while reducing saturation of fluorescent labels at features 16 as well as channel cross-talk. A control signal in the form of a variable voltage applied to each corresponding EOM 110a, 110b by a processor 220c, changes the polarization of the exiting light which is thus more or less attenuated by the corresponding polarizer 120a, 120b. Thus, each EOM 110 and corresponding polarizer 120 together act as a variable optical attenuator which can alter the power density of the light exiting from the attenuator. Hence each EOM 110 alters the power density of the interrogating light spot originating from one of lasers. Processor 220c has access to components of a type already described in connection with processor 220a of station 300 (and such components are numbered the same but with a "c" rather than an "a"), as well as to a display 228c and an array identifier reader 226c (which may, for example be a bar-code reader).

Each of the two beams provided on paths 130a, 130b then provide two spatially separated spots on an array 12 of an array unit 15 mounted on holder 200. These may be focused on front surface 11a directly without passing through substrate 10 when the array is being read with front surface 11a facing beam focuser 160 (that is, facing down in FIG. 4), or may be focused on front surface 11a after first passing through substrate 10 when the array is being read with front surface 11a facing away from beam focuser 160 (that is, facing up in FIG. 4). Various patterns for the spot separation can be used but the pattern of spots relative to one another will generally remain fixed unless independent optics were provided for the different beam paths 130. Note also that with the foregoing configuration the longer wavelength red light will generally be positioned to illuminate a given region of a feature before a spot of the shorter green light also tending to reduce triplet saturation as described in U.S. Pat. No. 6,320,196. As already mentioned, that patent is incorporated herein by reference in relation to the reading methods described therein.

Light emitted, in particular fluorescence, at two different wavelengths (for example, green and red light) from regions illuminated by the green and red interrogating light spots, in response to the interrogating light, is imaged using the same optics in focuser/scanner 160, and is reflected off mirror 156 and dichroic 154. The two different wavelengths are separated by a further dichroic mirror 158. There will be two paths of detection resulting from the spaced two interrogating light spots. As already mentioned though, for the sake of clarity these are only shown as one path in FIG. 5 up until mirror 158. Dichroic mirror 158 will direct red fluorescent light resulting from one interrogating light spot onto a detector 150a, while green fluorescent light resulting from another interrogating light spot will be directed onto detector 150b. More optical components (not shown) may be used between the dichroic and each of the two detectors 150 (such as lenses, pinholes, filters, fibers etc.) and each detector 150 may be of various different types (e.g. a photo-multiplier tube (PMT) or a CCD or an avalanche photodiode (APD)). All of the optical components through which light emitted from an array 12 in response to the illuminating laser light, passes to the two detectors 150, together with those detectors, form a detection system. This detection system has a fixed focal plane on the array 12 being read for a given position of the autofocus system (that is, in direction 196).

Instead of using dichroic 158, one can also use a design that images the different scanning spots onto different lightguiding fibers that then guide the signal from each one of these to a different detector. Such an arrangement for two scanning spots is described in U.S. Pat. No. 6,320,196.

In order to raster scan red and green interrogating light spots, the scanner is provided with a scan system. In this manner, each of the multiple features 16 of the array is read, with each read feature containing multiple pixels (for example, more than five, ten, or twenty). This can be accomplished by providing a housing 164 containing mirror 158 and focuser 160, which housing 164 can be moved in a first direction along a line (that is, from left to right or the reverse as viewed in FIG. 5) by a transporter 162. The second direction 192 of scanning (line transitioning) can be provided by second transporter which may include a motor and lead screw or belt (not shown) to move holder 200 along one or more tracks. The second transporter may use a same or different actuator components to accomplish coarse (a larger number of lines) movement and finer movement (a smaller number of lines). Of course, other scanning patterns could be used.

An autofocus detector 170 is also provided to sense any offset between different locations on array 12 when in the reading position, and a determined position of the focal plane of the detection system. An autofocus system includes detector 170, processor 220, and a motorized adjuster to move holder in the direction of arrow 196 (which may be referenced as a "z-axis" direction). A suitable chemical array autofocus system is described in U.S. Pat. No. 6,486,457.

Processor 220c of the apparatus is connected to receive signals from the detectors 150a, 150b. Each detector is part of another detection "channel". The signals in each channel are obtained at each of the two detected wavelengths from emitted light for each scanned pixel on array 12 when at the reading position mounted in holder 200. Processor 220c also receives the signal from autofocus offset detector 170, and provides the control signal to EOM 110, and controls the scan system. Processor 220c may also analyze, store, and/or output data relating to emitted signals received from detectors 150a, 150b in a known manner, as well as control the sensitivities of one or more of the four detectors.

Additionally processor 220c may retrieve an instruction (such as a sub-array pattern) on reading or processing signal data read from an array 12 of an array unit 15b received at reader station 90. These instructions may be retrieved by processor 220c from remote memory 224a through communication channel 280, using one or more test requests on a medium 364 also received at station 90 and the array identifier 356 of the array 12 of received array unit 15b (read by reader 226c). Test requests received on medium 364 can either be read by reader 226c (if the test requests are of a type suitable for such reading, for example a bar code) or read by an operator at station 90 and manually input by her through input device 230c. Alternatively, one or more of the instructions may be retrieved from a portable memory 324 received at station 90 in association with array unit 15b, using the one or more test requests and array identifier received as in the foregoing manner.

In the case where the instructions retrieved by processor 220c includes one or more sub-array patterns these may be used for masking so that signal data from an array being read at reader station 90 is acquired and saved from only features locations of one or more retrieved sub-array patterns. This can be accomplished by controlling EOMs 110 so as to only illuminate feature locations of one or more retrieved sub-array patterns. Alternatively, all features of the array being read can be illuminated but processor 220c discards all feature locations outside the one or more (or all) retrieved sub-array patterns and only saves in memory 234c the data from feature locations within one or more (or all) of the retrieved sub-arrays. In an alternative arrangement, signal data from all feature locations of an array being read at reader station 90 may be acquired and saved. However, a same signal processing method may be applied only to acquired signal data from feature locations of one or more retrieved sub-array patterns retrieved by processor 220c, as described further below. Reader station may also have the ability to render feature locations outside any or all retrieved sub-array patterns, incapable of producing signal data representative of sample component binding. This can be done by processor 220c predetermining a pattern of all such feature locations using the retrieved sub-array patterns and selectively bleaching all feature locations of the predetermined pattern by controlling EOM 110b and/or laser 100b to deliver sufficient power to such feature locations to bleach any fluorescent label there.

The components of the reader station 90 may all be contained within the same housing of a single same apparatus, or processor 220c and devices 222c through 230c may be a separate unit such as a standalone computer with the appropriate peripherals. One particular reader station is disclosed in U.S. Pat. No. 6,406,849. Another particular reader station that may be used is the AGILENT MICROARRAY SCANNER manufactured by Agilent Technologies, Palo Alto, Calif.

Continuing to refer to FIG. 5, another user station in the form of stand-alone station 400 is shown. This stand-alone station 400 includes a processor 220b which has access to various components of a same type as described in connection with processor 220c of reader station 90 (these same component types being numbered the same for stations 90, 400 except with an "c" or a "b"). Unlike reader station 90, stand-alone station 400 does not read arrays but instead may just receive and save signal data read from one or more arrays, each along with the associated identifier for the array (such as may be received over communication channel 280 or a portable storage medium 324). Station 400 may then function in the same manner as station 90 except station 400 does detect signal data from array features (nor can it bleach such features). Thus, reader station 90 can use an instruction retrieved from central station 300 based on an array identifier and test identifier, which instruction controls reading or processing the signal data read from an array. Station 400 on the other hand can only use retrieved instructions which control the processing (for example, feature extraction or data interpretation) of such signal data. Note that all of stations 90, 300, and 400 can be remote from one another, or all could be local to one another, or any combination of two of them could be local to one another while the other is remote.

One mode of operation of methods of the present invention will now be described with particular reference to the flowchart of FIG. 5. Reference numerals in parentheses refer to events shown in FIG. 5. Events within block 500 (shown as a broken line in FIG. 5) occur at the central data station 300 while the remaining events occur at reader station 90. It will be presumed that different arrays have already been fabricated, and that various tests for different arrays have been identified which tests require different instructions on reading or processing the signal data read from the array (for example, to use only a specified sub-array pattern). It will also be presumed that the foregoing information along with linked array identifiers and test requests for those tests have been saved in memory 234a such that each instruction for a test can be retrieved from memory 234a with a different combination of array identifier and test request. Alternatively, such information for each array unit 15 can be stored on a portable storage medium 324. It will also be assumed that these test requests are known to individuals who might wish one or more such tests, such as a result of the test types being of common descriptors in a research lab or doctor's office, or elsewhere or such information otherwise being made available to those locations (through publications, advertisements, internet, and the like). Multiple packages 340 each containing an array unit 15b previously exposed to a sample, a medium 364 carrying one or more test requests, and any associated portable storage medium 324 (associated as a result of being in a same package), may have already been provided to reader station 90. The test or tests which are to be performed by the sample exposed array are recorded as one or more test requests on test request medium 364, which may be a piece of paper, order form, or portable memory. The test requests may simply be written as to the type of test desired or may be a reference to a test identifier (such as a unique code). The individual may additionally include on medium 364 an identification of a source of the sample (such as an individual patient's identification, for example Social Security Number, patient name, and the like) to which the array had been exposed.

Referring particularly to FIG. 5, at the array reader station 90 the sample exposed array is received (510) in package 340 with the test request(s) on medium 364 or optionally on portable storage medium 324 (all associated with one another by being in the same package 340). The array identifier is read (520) using reader 226c, and the test request is read (520) by an operator and input to processor 220c through device or read by reader 226c. A determination (530) is then made as to whether array signal data from the sample exposed array will be read or processed at reader station 90 in accordance with an instruction required for the requested test, or whether reader station 90 will simply read all signal data from the sample exposed array and have a remote location perform processing in accordance with such an instruction. If the answer to determination (530) is YES, then processor 220c may transmit (560) the array identifier, test request, and any payment information to the central data station 300. This payment information may identify an account for reader station 90, an operator there, someone who originally completed the test request on medium 364, an individual from which the sample to which the array was exposed was derived, or some other entity. If the answer to determination (530) is NO, then processor 220c may simply proceed to read (540) all signal data from the array and transmit (550) all read signal data, test request, and any account information as previously described, to central data station 300.

Continuing to refer to FIG. 5, the information transmitted from reader station 90 is received (570). As apparent from above, this received information may or may not include the read signal data from the user station (such as reader station 90 or stand-alone station 400). The received array identifier and test request are then used to retrieve (580) the instruction from memory 234a which is specific to that test request. As mentioned previously such a retrieved instruction for a specific test request and array identifier combination, may include a sub-array pattern, or an instruction on processing read signal data such as a data processing module (for example, feature extraction, data interpretation, or one or more parameters for such a data processing module).

A determination (590) is then made as to whether the retrieved instruction will be applied at the central data station 300 or applied at the reader station 90. This determination can either be based on a specific request in the data received along with the array identifier, test request, and account information, or can be based on the assumption that application of the instruction at central station 300 is requested when read signal data from the array is received (570). Alternatively, this determination can be made based on the test request itself and/or array identifier received. For example, memory 234a may contain a list of test requests which will always be performed at data station 300 which processor 220a checks against the received test request. In this case if read signal data was not received along with the received test request and array identifier (or otherwise associated therewith) processor 220a can transmit a rejection of the test request or request for the read signal data to reader station 90.

If the result of the determination (590) is that the retrieved instruction will be applied at the data station 300 (YES result), then the received array signal data is processed (600) using the retrieved instruction. The result is then transmitted (610) to reader station 90 or any other location that might have been specified in instructions received along with other information received (570), where it is received (620) for further use as desired there. If the result of the determination (590) is that the retrieved instruction will be applied at reader station 90 (NO result), then the instruction is transmitted (630) there where it is received (650). At array station 90, the array signal data is then read or processed in accordance with the retrieved instruction. Optionally, array station 90 may also render feature locations not required by any received instruction, incapable of producing signal data representative of sample component binding by bleaching such features with a laser of the apparatus. Such features may be those which are outside any retrieved sub-array. This provides a measure of security to prevent signal data being later acquired from features irrelevant to the requested test or tests, and misused. Note that in any event when the result or retrieved instruction is transmitted (610 or 630) the account for which information was received (570) is then charged with an amount based on the test request received (570) with the account. This amount may be different for different combinations of array identifier and test request, and discounts may be given for different test requests (for example, multiple test requests which use multiple arrays) or volume of test requests from a same station 90 or for a same individual identified in the data received (570).

At a later time, processor 220c can determine (660) if a new request for signal data associated with a particular array identifier is desired. This new request could be the result of receiving another medium 364, or may be initiated by an operator at station 90, or received in a transmission from some other location (remote or local). For example, an array fabricator or someone else may have determined that a new test requiring a different instruction is possible for a previously fabricated array. The new test request, array identifier, and instruction, may all be saved in memory 234a at central data station 300 (such as by transmitting to station 300 over channel 280). If the result of determination (660) is NO, the loop can cycle as often and as for as long as might be desired. If the result of the determination (660) is YES, then the entire process can be repeated one or more times beginning with event (520) except that it may not be necessary to again read (520) the array identifier or new test request. In this manner, as new tests become available for a given array, new test results can be obtained on previously obtained signal data without the need to obtain another sample, expose it to another array, and read that array.

With regard to stand-alone station 400, as already mentioned this may have received read array signal data for one more arrays, along with associated array identifiers, form array reader station or elsewhere. A test request for an array may also have been received from any of those locations or elsewhere, or may be selected at station 400. Station 400 may then interact with station 300 in the same manner as station 90 illustrated in FIG. 5. However, in this case events (510, 520) are optional at station 400. Furthermore, stand-alone station 400 can only receive and implement instructions based on the array identifier and test request combination, which do not relate to reading of the array (since station 400, unlike station 90, does not have an array reading system).

As to the different instructions for each particular array identifier/test request combination which may be retrieved (580) from memory 234a, as mentioned above these can include a sub-array pattern such as sub-arrays 82 shown in FIG. 4. Such an instruction can be used at station data station 300 or reader station 90 in the masking or other methods as already described. In addition, different signal processing methods can be applied to saved data for different retrieved sub-array patterns. For example, as mentioned above the same signal processing method may be an encryption method based on a key, and an encryption method based on a different key is applied to signal data acquired from feature locations of a different retrieved sub-array pattern or also to feature locations outside any retrieved sub-array pattern. In this manner access to different results can be readily controlled by providing to an individual only the key(s) to results from one or more sub-arrays as desired.

Instructions for processing read signal data for each particular array identifier/test request combination which may be retrieved, may also include data processing instructions in the form of computer program code, such as one or more feature extraction modules or one or more parameters for a feature extraction program. Examples of feature extraction programs for which instructions or parameters may be provided, include methods or any part of them such as those described in U.S. patent application Ser. No. 10/077,446 titled "Method And System For A Range Of Automatic, Semi-Automatic, And Manual Grid Finding During Feature Extraction From Molecular Array Data", or Ser. No. 09/589,046 "Method And System For Extracting Data From Surface Array Deposited Features", or U.S. Pat. No. 5,721,435, all incorporated herein by reference. Following or before feature extraction, details of the array layout can be retrieved using the read array identifier 356 in a manner similar to that described in U.S. Pat. No. 6,180,351.

Similarly, instructions for processing read signal data for each particular array identifier/test request combination which may be retrieved, may further include data processing instructions in the form of computer program code (such as a program module), or one or more parameters for a computer program which performs array signal data processing (such as array signal data interpretation). Array signal data processing programs attempt to interpret the array signal data in a manner which aids in understanding the significance or meaning of the data. Examples of such array data interpretation programs are those which execute methods such as those described in U.S. Pat. No. 5,965,352, U.S. Pat. No. 6,132,969, U.S. Pat. No. 6,212,122, U.S. Pat. No. 6,222,093, U.S. Pat. No. 6,324,479, U.S. Pat. No. 6,303,291, and elsewhere. Any results of methods of the present invention may then be used to make an assessment if one or more targets is present in a sample to which the array was exposed, or whether an organism from which the sample was obtained exhibits a particular condition (for example, cancer). The results may be further forwarded or transmitted to a remote location at which they are received, and can be re-transmitted to elsewhere from that location as desired.

As mentioned previously the retrieved instruction for a specific test request and array identifier combination, may include a sub-array pattern, or an instruction on processing read signal data such as a data processing module. Another form of the instruction may be a decryption key in the situation where all data read from the array by the reader is automatically encrypted by the processor 220. In this case the encryption key would automatically only decrypt the data from those features which is required for the requested test. In another embodiment the features of an array from which read signal data is required for a requested test may be located differently between different arrays or different batches of arrays, where the features on such arrays are otherwise the same but arranged differently on those arrays or batches of arrays. In this case, the instruction would identify the location of the features from which data is required for the requested test.

Additional instructions required for further tests can be added over time to the memory (such as memory 234a) in which such instructions are saved. This allows users the ability to select from additional tests from a given array without change to the array itself.

In one embodiment, arrays may be provided to users free of charge with a charge made to a user's (or other's) account, or a request for payment generated, only in response to the user forwarding the test request. In this manner, a user is only charged for the test or tests requested by them. In any situation, the amount charged to an account, or for which a payment request is generated, may be based on the number of tests requested by a given user (or class of users, such as all the user's in a same company) from a particular array or arrays. For example, a user could be given a reduction in the additional cost for further tests requested from the central or stand-alone station, for a particular array beyond the first test request, which reduction could increase with an increasing number of tests requested from a particular array. Of course in any embodiment the amount charged to an account or for which a payment is requested need could be credited to different parties' accounts in various manners (whether paid immediately upon crediting or not). For example, the entire amount may be credited to an array fabricator's account. Alternatively, a third party may design a test and an instruction required by that test on the reading or processing the signal data read from the array. In this case, the amount may be credited to the array fabricator's account and that of the third party in any suitable prearranged proportion. In a further variation quality control features can be included in an array and the instruction for the requested test only causes an amount to be charged to an account or payment requested for that test, when read signal data from the quality control features indicates that a reliable result for the requested test was obtained from the array. The instruction can cause this charge or payment requesting by, for example, communicating to the central or stand-alone station that signal data read from the quality control features indicates a reliable result for the requested test was obtained from the array.

Various and modifications to the particular embodiments described above are, of course, possible. Accordingly, the present invention is not limited to the particular embodiments described in detail above.

What is claimed is:

1. A method comprising:
providing a test request for reading or processing signal data from a sub-array of probes on a chemical array, wherein the test request references a type of test to be performed;
retrieving an instruction, corresponding to the test request provided, from a plurality of instructions stored in a memory, wherein different instructions for reading or processing signal data from the chemical array, corresponding to different test requests are stored in the memory, each instruction retrievable with a different test request, based on the test request provided and wherein at least two of said instructions instruct processing or reading a sub-array pattern, different from the other, from the same chemical array, and wherein any sub-array pattern, whether comprising a continuous set of features or a non-continuous set of features is instructable;
reading or processing the signal data, for the sub-array instructed by the retrieved instruction; and
outputting results from said reading or processing for use by a user.

2. A method according to claim 1, additionally comprising repeating the providing, retrieving, and reading or processing one or more times with respect to the chemical array, each time with a different test request, and wherein the retrieving comprises retrieving different instructions in at least one repetition, and reading or processing signal data from a different sub-array in at least one of the repetitions.

3. A method according to claim 1 wherein at least one of said instructions comprises an instruction for processing signal data from the sub-array of the chemical array identified by a sub-array pattern provided by the instruction.

4. A method according to claim 3 wherein at least one of said instructions comprises an indication that only signal data from feature locations in the sub-array need be read or processed.

5. A method according to claim 3 wherein the sub-array pattern is received from a memory which carries multiple sub-array patterns for the chemical array, each said sub-array pattern being retrievable with a different test request.

6. A method according to claim 5 wherein said processing the signal data comprises processing only signal data from features within the received sub-array pattern, as applied to the chemical array.

7. A method according to claim 5, further comprising transmitting results from acquired signal data from only those array feature locations within the received sub-array pattern, wherein those array feature locations are identified by applying the received sub-array pattern to the chemical array.

8. A method according to claim 7 wherein the results do not provide any indication of which feature locations of the chemical array are bound to a sample component.

9. The method of claim 1, further comprising providing an array identifier, said array identifier identifying the chemical array, and wherein said retrieving an instruction is performed based on said test request and said array identifier.

10. The method of claim 1, further comprising providing account information in addition to said providing a test request.

11. The method of claim 10, further comprising charging an account according to said account information provided, for a test requested by said test request having been provided.

12. The method of claim 1, further comprising transmitting results of said processing to a user at a remote location.

13. The method of claim 1, wherein the at least one instruction comprises an indication that only signal data from feature locations in the sub-array need be read or processed.

14. The method of claim 10, additionally comprising providing to a requestor of the test a price for the test requested.

15. The method of claim 1, wherein at least one instruction comprises an instruction on processing read signal data.

16. The method of claim 1, wherein at least one instruction comprises a data processing instruction or a parameter for a method which performs array signal data interpretation.

17. The method of claim 1, wherein said signal data is obtained from labeled target molecules bound to one or more probes on the chemical array.

18. The method of claim 1, further comprising providing a unique array identifier for the chemical array with said test request, wherein said different instructions for reading or processing signal data from the chemical array are each linked with a different test request and are all linked to the unique array identifier.

19. The method of claim 1, wherein said reading or processing are carried out at a first location, said test request is transmitted to a second location remote from said first location, and the instruction is retrieved at said second location and transmitted to said first location.

20. The method of claim 1, wherein signal data from the chemical array and said test request are transmitted from a first location to a second location remote from said first location, and wherein said reading or processing the signal data comprises processing the signal data at said second location.

21. The method of claim 11, wherein said reading or processing are carried out at a first location, and said test request and account information are transmitted to a second location remote from said first location.

22. The method of claim 11, wherein signal data from the chemical array and said test request and account information are transmitted from a first location to a second location remote from said first location, and wherein said reading or processing the signal data comprises processing the signal data at said second location.

23. The method of claim 1, wherein said test request is transmitted form a first location to a second location remote from said first location, said method further comprising transmitting a quoted price for the test requested, from said second location to said first location.

24. The method of claim 1, wherein said outputting comprises presenting said read or processed data on a display for viewing by a human user.

25. The method of claim 1, wherein said test request is selected from the group of test requests consisting of: tests for expression levels of one or more genes or a class of genes; tests for gene polymorphisms, tests for copy numbers of one or more genes or a class of genes; tests for the presence of a pathogen; and tests for a disease condition of an organism from which a sample exposed to the chemical array was derived; testing a sample to ascertain whether it contains one or more predefined components, either quantitatively or qualitatively.

26. The method of claim 1, wherein a sample has been exposed to the chemical array prior to said reading or processing the signal data, and wherein said result indicates whether a sample that was exposed to the chemical array likely does or does not exhibit a particular condition selected from the group consisting of: a disease, presence of a pathogen and a particular genetic deficiency.

27. A method comprising:
providing a test request for reading signal data from a sub-array of probes on a chemical array, wherein the test request references a type of test to be performed;
retrieving an instruction, corresponding to the test request provided, from a plurality of instructions stored in a memory, wherein different instructions for reading signal data from the chemical array, corresponding to different test requests are stored in the memory, each instruction retrievable with a different test request, based on the test request provided and wherein at least two of said instructions instruct processing or reading a sub-array pattern, different from the other, from the same chemical array;
reading the signal data, for the sub-array instructed by the retrieved instruction; and
outputting results from said reading for use by a user.

28. A method comprising:
providing a test request for reading or processing a sub-array of probes on a chemical array, wherein the test request references a type of test to be performed;
retrieving an instruction, corresponding to the test request provided, from a plurality of instructions stored in a memory, wherein different instructions for reading or processing signal data from the chemical array, corresponding to different test requests are stored in the memory, each instruction retrievable with a different test request, based on the test request provided and wherein at least two of said instructions instruct processing or reading a sub-array pattern, different from the other, from the same chemical array;
reading signal data, for the sub-array instructed by the retrieved instruction or exposing the sub-array to a sample; and
outputting results from said reading for use by a user or providing the exposed array.

\* \* \* \* \*

UNITED STATES PATENT AND TRADEMARK OFFICE
CERTIFICATE OF CORRECTION

| | |
|---|---|
| PATENT NO. | : 7,353,116 B2 |
| APPLICATION NO. | : 10/633611 |
| DATED | : April 1, 2008 |
| INVENTOR(S) | : Webb et al. |

Page 1 of 1

It is certified that error appears in the above-identified patent and that said Letters Patent is hereby corrected as shown below:

In column 22, line 46, in Claim 23, delete "form" and insert -- from --, therefor.

Signed and Sealed this

Nineteenth Day of August, 2008

JON W. DUDAS
*Director of the United States Patent and Trademark Office*